United States Patent [19]

Savoly et al.

[11] Patent Number: 5,158,612
[45] Date of Patent: Oct. 27, 1992

[54] FOAMING AGENT COMPOSITION AND PROCESS

[75] Inventors: Arpad Savoly, Martinsville; Dawn P. Elko, Flemington, both of N.J.

[73] Assignee: Henkel Corporation, Ambler, Pa.

[21] Appl. No.: 783,059

[22] Filed: Oct. 25, 1991

[51] Int. Cl.⁵ ............... C04B 22/14; C04B 11/024
[52] U.S. Cl. .................... 106/678; 106/680; 106/781; 252/308; 156/39; 156/43
[58] Field of Search .............. 264/43; 106/678, 680, 106/781; 252/308; 156/39, 43

[56] References Cited

U.S. PATENT DOCUMENTS

| | | | |
|---|---|---|---|
| 4,156,615 | 5/1979 | Cukier | 106/111 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,453,022 | 6/1984 | McCain et al. | 568/618 |
| 4,618,370 | 10/1986 | Green et al. | 106/111 |
| 4,676,835 | 6/1987 | Green et al. | 106/111 |
| 4,678,515 | 7/1987 | Green et al. | 106/111 |

FOREIGN PATENT DOCUMENTS 2196334 4/1988 United Kingdom .

*Primary Examiner*—Karl Group
*Assistant Examiner*—Paul Marcantoni
*Attorney, Agent, or Firm*—Ernest G. Szoke; Wayne C. Jaeschke; Real J. Grandmaison

[57] ABSTRACT

Narrow range alkoxylated alcohols are sulfonated and used as improved foaming agent compositions. These compositions exhibit desirable foaming characteristics for use in the manufacture of gypsum board and concrete and in oil field applications.

16 Claims, No Drawings

FOAMING AGENT COMPOSITION AND PROCESS

BACKGROUND OF THE INVENTION

1. Field of the Invention

This invention relates to compositions useful for generating foam and more particularly to compositions for use in foaming agents during, for example, the manufacture of gypsum board or concrete, and to processes for using such compositions.

2. Statement of Related Art

Generally, gypsum board consists of a core of set gypsum surfaced with paper or other fibrous material suitable to receive a coating such as paint. It is common to manufacture gypsum board by placing an aqueous core slurry ("slurry") composed predominantly of calcined gypsum between two sheets of paper thereby forming a board. The resultant core is allowed to set or harden by rehydration of the calcined gypsum, usually followed by heating the gypsum board in a dryer so as to drive away any excess water.

It is common practice to introduce air bubbles into the slurry to reduce its density and to reduce the amount of water necessary to produce a workable slurry. This is normally achieved by the addition of a foaming agent, comprised of an active ingredient along with other additives, during the formation of the slurry or by adding externally-generated foam to the slurry. The externally-generated foam is normally produced by incorporating air or other gas into an aqueous solution of a foaming agent; the resulting mixture is then mixed with the slurry.

Foaming agents generally contain as active ingredients one or more salts of alkyl ether sulfates. Known salts of alkyl ether sulfates employed in foaming agents, such as those disclosed in Cukier U.S. Pat. No. 4,156,615, Green et al. U.S. Pat. Nos. 4,618,370, 4,676,835 and 4,678,515, and UK published patent application GB 2 196 334 have the general formula I:

$$CH_3(CH_2)_xCH_2(OCH_2CH_2)_yOSO_3^-M^+ \quad (I),$$

where x and y represent integers which may be the same or different and may have non-integral average values in any practical sample size because of the method of synthesis, and $M^+$ represents either sodium or ammonium ion.

In a practical mixture of such foaming agents as commercially used, the distribution of molecules having particular numbers of ethoxy units, as represented by y in formula I, can be represented in the form of a generally bell-shaped curve in which the number or fraction of molecules containing a particular number of ethoxy unit is plotted versus the number of such ethoxy units, starting at y=0 (representing unethoxylated starting material). The broader the curve, the more evenly distributed are values of y. The narrower the curve, the more narrowly distributed are values of y. Methods are available for separating compounds of formula I having specified values of x and y from compounds having other values of x and/or y, but these methods are tedious and expensive and are not believed to be used in industrial practice.

Accordingly, an object of this invention is to provide practicable compositions in which the individual molecules in the composition conform to formula I or a similar formula but the distribution of values of y in the mixture is more favorable for foaming than in the mixtures available heretofore.

DESCRIPTION OF THE INVENTION

In this description, except in the working examples and claims and wherever expressly indicated to the contrary, all numerical specifications of amounts of materials or conditions of reaction or use are to be understood as modified by the term "about" in describing the broadest scope of the invention. Practice of the invention within the exact numerical limits given is generally preferred.

SUMMARY OF THE INVENTION

It has been found that compounds of formula I having preferred values for x and y exhibit enhanced foaming characteristics. The presence of substantial fractions of molecules with less preferred values for x and y disadvantageously tends to decrease foaming characteristics. It has also been found that sulfation of certain selected commercially available products generally described as "narrow range alkoxylated alcohols" produces mixtures of compounds extraordinarily valuable as foaming agents. Accordingly, one embodiment of the invention is a mixture of molecules, each of which conforms to the general formula II:

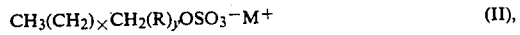

$$CH_3(CH_2)_xCH_2(R)_yOSO_3^-M^+ \quad (II),$$

where x and y represent integers which may be the same or different and may have non-integral average values in any practical sample size, R represents an alkoxyl group, and $M^+$ is chosen from the group consisting of sodium and ammonium ions. Unalkoxylated compounds are represented by y=0. In compositions according to the invention, x has an average value ranging from 4 to 10 with preferred average values of x ranging from 6 to 8; y has an average value ranging from 0 to 5, a preferred average value ranging from 1 to 4, and a more preferred average value ranging from 2 to 3.

These compositions according to the invention are further characterized by a narrow distribution of values of y, i.e., a higher percentage of compounds having values of y near preferred values of y. (Percentages are specified herein by weight unless otherwise stated.) Specifically, with increasing preference in the order stated for each value of y, with independent preference for each stated value of y, and with percentages referred to the total amount of molecules conforming to formula II in the foaming agent composition according to the invention: not more than 20%, 17%, 11%, or 9% of the molecules have a value of y=0; and at least 45%, 46%, 47%, 48%, 49%, 50%, 51%, or 52% of the molecules have y=2 or 3.

Reaction products of alcohols and alkylene oxides which have a narrow or peaked distribution of alkoxy units ("narrow range alkoxylated alcohols") that are suitable as starting materials for making these compositions according to the invention are known. See for example, McCain et al. U.S. Pat. No. 4,453,022, Yang et al. U.S. Pat. No. 4,210,764, Yang et al. U.S. Pat. No. 4,223,164, and Yang et al. U.S. Pat. No. 4,239,917.

It has been found that sulfating suitable narrow range alkoxylated alcohol mixtures yields a composition of mixed compounds, each individually characterized by formula II, which exhibit desirable foaming characteristics despite the presence of some molecules having less preferred numbers of alkoxy units, including the highly unpreferred number zero. Separation of preferred compounds from less preferred compounds is not required to obtain superior foaming agents.

Another embodiment of the invention is a foaming agent, in which the narrow range alkyl ether sulfate mixtures according to the present invention as already described above constitute between 40% and 60% of the total foaming agent composition; the other components of the foaming agent composition being a hydrotrope, water, and optionally, a chelating or sequestering agent for divalent and higher valent metal ions. The latter constituent is particularly valuable when the foaming agent is made up with hard water and the chelating agent effectively sequesters calcium and magnesium ions. A hydrotrope comprises 5% to 20% of a foaming agent composition according to the invention; the hydrotrope is preferably selected from the group consisting of methanol, ethanol, isopropanol, ethylene glycol, propylene glycols, polyethylene and polypropylene glycols, monoalkyl ethers of ethylene glycol, alkyl polyglucosides, and the like, and mixtures thereof. The balance of the foaming agent composition is water.

Further embodiments of the invention are methods of using the foaming agent compositions described above in the manufacture of gypsum board. Use of the narrow distributions of preferred alkoxy compounds of formula II in foaming agent compositions in the manufacture of cement or concrete and in oil well applications are also contemplated as other embodiments of the invention.

DESCRIPTION OF PREFERRED EMBODIMENTS OF THE INVENTION

For economic reasons, it is preferred, with increasing preference in the order given, that compositions according to the invention contain at least 10, 12, 15, or 17% by weight, referred to the total content of molecules conforming to formula II, of molecules in which y in formula II has each of at least two different integral values.

In compositions according to the invention, x in formula II has values ranging from 4 to 10 with preferred values ranging from 6 to 8 and with a preferred average value for x being 7; R in formula II is preferably ethoxy or propoxy, most preferably ethoxy; y in formula II has values ranging from 0 to 5, preferred values ranging from 1 to 4, more preferred values ranging from 1 to 3, still more preferred values from 2 to 3. In one preferred embodiment, the composition is characterized by an average value of y=2.2. $M^+$ in formula II represents either sodium or ammonium ions, with ammonium ions being preferred.

In the manufacture of gypsum particle board according to this invention, foaming agent compositions of the present invention as described above are normally added to a foam generator in the form of an aqueous solution in which the concentration of the narrow range mixtures of alkyl ether sulfates in aqueous solution is preferably in the range of 0.01% to 0.90%. The resultant foam is then mixed with the aqueous core slurry in water. The resultant foam preferably comprises 2% to 20% by weight of the aqueous core slurry for the particle board.

Further appreciation of the present invention may be had from considering the following examples and comparative examples which are intended to illustrate, but not limit, the invention.

EXAMPLES AND COMPARISON EXAMPLES

Analysis of Ethoxylated $C_8/C_{10}$ Alcohols

Analysis of a sample of typical commercially available $C_8/C_{10}$ ethoxylated alcohols (Item 1) and of samples of two typical commercially available $C_8/C_{10}$ narrow range ethoxylated alcohols particularly suitable for this invention (Items 2 and 3) provides the results shown in Table 1.

TABLE 1

| Item No. | Weight % in Item of Molecules with Number of Ethoxy Units per Molecule Equal to: | | | | | |
|---|---|---|---|---|---|---|
| | 0 | 1 | 2 | 3 | 4 | 5 |
| 1 | 32 | 28 | 26 | 13 | 1 | 0 |
| 2 | 9 | 12 | 24 | 29 | 20 | 6 |
| 3 | 17 | 29 | 35 | 17 | 2 | 0 |

The above data indicate that the narrow range ethoxylated alcohols have a higher percentage of molecules with mole amounts of ethoxy units at values of 2 and 3 and a significantly lower percentage of undesirable unethoxylated alcohols. These differences in percentages make the narrow range ethoxylated alcohols more desirable precursors for foaming agents.

Sulfating Narrow Range Ethoxylated Alcohols

Narrow range ethoxylated alcohols that are suitable starting materials for making the compositions of this invention may be sulfated using standard techniques well known to those skilled in the art. An example is provided below.

One mole of narrow range ethoxylated alcohol was placed in a glass lined reactor vessel and vacuum stripped of moisture so that less than 0.1% moisture remained. The reactor was then cooled to 25°–28° C. While maintaining the temperature at about 25°–30° C. and under a high vacuum, 1.0–1.1 mole of chlorosulfonic acid was added to the reactor vessel. The resultant hydrochloric acid formed was then removed by vacuum stripping until no more gas evolved, indicating reaction completion. The fluid contents of the reactor vessel were then removed and introduced into another vessel containing an effective amount of water, alcohol and alkali to neutralize the fluid to a neutral pH and convert it into a suitable foaming agent according to this invention.

Distribution of x and y Values in Formula II for Examples 1–2 ("Items 2–3") and Some Comparison Examples Table 2 shows the percentage of molecules with various values of the indices x and y from formula II in sulfates made from Items 1–3 shown in Table 1 (and identified with the same Item numbers in Tables 2–5) and in some commercially available foaming agents that serve as comparison examples. (Because of obligations under secrecy agreements between the applicants and the suppliers of these commercial products, the commercial names of the comparison example products are not being disclosed. Instead, the products are designated by letters below.) The percentages were determined by conventional gas chromatography—mass spectrometry (GC-MS). Percentages of molecules having 6 ethoxy units or more were not included in the table but were always small.

TABLE 2

| Foaming Agent Identification | Value of x in Formula II | Percent in Total Mixture of Molecules Conforming to Formula II with Values of y Equal to: | | | | | |
|---|---|---|---|---|---|---|---|
| | | 0 | 1 | 2 | 3 | 4 | 5 |
| Product A | 6 | 2.4 | 0.0 | 0.0 | 0.0 | 0.0 | 0.0 |
| | 8 | 13.3 | 14.4 | 17.9 | 15.6 | 8.6 | 2.2 |
| | 10 | 4.0 | 3.8 | 4.4 | 3.8 | 1.9 | 0.0 |
| (Branched) | 10 | 3.2 | 1.6 | 1.5 | 1.2 | 0.0 | 0.0 |
| Totals | | 22.8 | 19.8 | 23.9 | 20.5 | 10.4 | 2.2 |
| Item 1 | 6 | 11.3 | 12.2 | 10.2 | 4.2 | 0.0 | 0.0 |
| | 8 | 20.0 | 16.0 | 15.4 | 8.4 | 1.3 | 0.0 |
| | 10 | 0.9 | 0.0 | 0.0 | 0.0 | 0.0 | 0.0 |
| Totals | | 32.2 | 28.2 | 25.6 | 12.6 | 1.3 | 0.0 |
| Product B | 6 | 1.0 | 0.7 | 0.8 | 0.4 | 0.0 | 0.0 |
| | 8 | 9.1 | 11.4 | 16.2 | 15.1 | 10.3 | 3.4 |
| | 10 | 4.9 | 1.4 | 1.6 | 1.4 | 0.7 | 0.0 |
| (Branched) | 10 | 4.9 | 4.5 | 3.3 | 0.0 | 0.0 | 0.0 |
| | 12 | 3.0 | 1.0 | 1.1 | 0.9 | 0.0 | 0.0 |
| Totals | | 22.9 | 19.0 | 23.0 | 17.8 | 11.1 | 3.4 |
| Product C | 4 | 0.0 | 0.8 | 0.0 | 0.0 | 0.0 | 0.0 |
| | 6 | 8.2 | 10.4 | 9.1 | 6.7 | 4.1 | 1.5 |
| | 8 | 20.3 | 13.8 | 11.4 | 7.6 | 4.1 | 0.8 |
| | 10 | 0.7 | 0.0 | 0.0 | 0.0 | 0.0 | 0.0 |
| Totals | | 29.2 | 25.0 | 20.5 | 14.3 | 8.2 | 2.4 |
| Product D | 6 | 14.9 | 12.1 | 8.0 | 4.6 | 1.8 | 0.5 |
| | 8 | 25.2 | 15.5 | 10.3 | 4.7 | 1.7 | 0.0 |
| | 10 | 0.7 | 0.0 | 0.0 | 0.0 | 0.0 | 0.0 |
| Totals | | 40.8 | 27.6 | 18.3 | 9.3 | 3.6 | 0.5 |
| Product E | 6 | 4.7 | 8.3 | 9.4 | 7.9 | 3.9 | 1.1 |
| | 8 | 25.2 | 15.5 | 19.3 | 4.7 | 1.7 | 0.0 |
| | 10 | 0.7 | 0.0 | 0.0 | 0.0 | 0.0 | 0.0 |
| Totals | | 30.6 | 23.8 | 28.7 | 12.6 | 5.7 | 1.1 |
| Item 2 | 6 | 2.4 | 4.3 | 10.3 | 13.4 | 9.1 | 2.8 |
| | 8 | 6.6 | 7.2 | 13.6 | 15.6 | 10.9 | 4.0 |
| | 10 | 0.0 | 0.0 | 0.0 | 0.0 | 0.0 | 0.0 |
| Totals | | 9.0 | 11.5 | 23.8 | 28.9 | 20.0 | 6.0 |
| Item 3 | 6 | 4.6 | 10.9 | 13.6 | 6.1 | 0.8 | 0.0 |
| | 8 | 10.3 | 15.3 | 17.8 | 9.7 | 1.3 | 0.0 |
| | 10 | 2.3 | 2.7 | 3.1 | 1.4 | 0.0 | 0.0 |
| Totals | | 17.3 | 28.9 | 34.6 | 17.2 | 2.1 | 0.0 |

Notes for Table 2
The line in some of the groups preceded by (Branched) indicates material that does not conform strictly to Formula II; instead, two of the —$CH_2$— units prescribed by that formula are substituted by a —$CH(CH_3)$— unit. Molecules of this type, which are present in some of the Comparison Examples but not in the Examples according to the invention, are considered as part of "Total Mixture of Molecules Conforming to Formula II" for the purposes of computing the percentages in this Table. Where no line preceded by (Branched) appears in a group in the Table, the item contains less than 0.0% of any such material. Where no line for x = 12, appears, the sample also contains less than 0.0% of any material with x = 12.

Some of the data contained in Table 2 are presented in a different form for more convenient comparison to Table 3.

TABLE 3

| Foaming Agent Identification | Percent in Total Mixture of Molecules Conforming to Formula II with Values of y = | |
|---|---|---|
| | 0 | 2 or 3 |
| Product D | 40.8 | 27.6 |
| Item 1 | 32.2 | 38.2 |
| Product E | 30.6 | 41.3 |
| Product C | 29.2 | 34.7 |
| Product B | 22.9 | 40.8 |
| Product A | 22.8 | 44.3 |
| Item 3 | 17.3 | 52.7 |
| Item 2 | 9.0 | 52.7 |

As can be readily seen from the above data for Items 2 and 3, the compositions of the present invention comprise a greater percentage of desirable molecules having 2 or 3 alkoxy units per molecule and a lesser percentage of undesirable unethoxylated molecules. This combination yields desirable foaming characteristics. A preferred composition has an average of 2.2 ethoxy units per molecule. Some of the improved foaming characteristics are indicated by the tests and data set forth below.

FOAMING CHARACTERISTIC TESTING

Laboratory scale experiments were carried out to compare foaming characteristics of the various commercially available foaming agent compositions and Item 1 (comparison examples) with Item 2 according to the present invention.

TEST PROCEDURE I

This procedure was used to compare the densities of slurries suitable for gypsum board manufacture. The equipment required for Test Procedure I included a Hamilton Beach blender connected to a rheostat, and a CT-60 Cement Cube Mold, commercially available from Soiltest Inc., Pennsauken, N.J.

A slurry was prepared by combining 500 grams of stucco, 380 grams of distilled water, 0.5% (measured as solids on weight of stucco solids) of DILOFLO ™ GB dispersant, 0.02% (measured as solids on weight of stucco solids) of retardant, and 0.025% (measured as solids on weight of stucco solids) of foaming agent to produce a 0.76:1 water to stucco ratio. (The amount of stucco and water used must be adjusted in order to account for the solids and water in the dispersant.)

The test procedure began by weighing the stucco in a beaker separate from other slurry components. The distilled water, dispersant, and retardant were respectively weighed into the blender cup. The stucco was then poured into the blender cup and the slurry mixed for 5 seconds. The foaming agent of the present invention was then weighed into the blender cup and the slurry was mixed for 30 seconds.

A three cube CT-60 Cement Mold was then separately weighed. It should be noted that the mold is thinly coated With Potters ™ 14A which facilitates the removal of a cube from its mold after hardening. The slurry was poured into the first cube. Using a spatula, the stucco was scraped in order to even its surface with the mold surface. The weight of the mold and stucco was then recorded.

The weighing process was repeated for the second and third cubes of the CT-60 Cement Mold and the weight of each was recorded. The average weight of the three cubes was recorded as the wet pour weight and was used for comparison purposes as indicated in the following table. The cubes were allowed to harden at room temperature for approximately one hour and were then removed from their molds. Each cube was reweighed and the average was taken of all three cubes. The average weight was recorded as the dry weight of the cubes. The cubes were then placed in an oven set at a temperature of 190° C. and allowed to completely dry. The cubes were subsequently removed and allowed to cool. The cubes were reweighed and the average weight of all three was determined. The weight was recorded as the after oven drying weight at 190° C. The cubes were stored in a desiccator. Each cube was reweighed an additional time before being submitted to the Physical Testing Laboratory for compressive strength tests.

Table 4 summarizes the percent increase of foaming

TABLE 4

| Foaming Agent | Initial Wet Weight | Density g/cm³ | % Foam Increase |
| --- | --- | --- | --- |
| Item 1 | 161.7 | 1.23 | 20.9 |
|  | 162.7 | 1.24 |  |
|  | 163.8 | 1.25 |  |
| Product D | 160.8 | 1.23 | 21.3 |
|  | 162.4 | 1.24 |  |
|  | 162.4 | 1.24 |  |
| Product A | 160.4 | 1.22 | 21.4 |
|  | 160.8 | 1.23 |  |
|  | 163.8 | 1.25 |  |
| Product C | 159.1 | 1.21 | 21.7 |
|  | 161.6 | 1.23 |  |
| Product B | 158.2 | 1.21 | 22.2 |
|  | 160.2 | 1.22 |  |
|  | 161.6 | 1.23 |  |
| Product E | 157.1 | 1.20 | 22.7 |
|  | 160.0 | 1.22 |  |
|  | 159.8 | 1.22 |  |
| Item 2 | 154.6 | 1.18 | 24.8 |
|  | 154.1 | 1.18 |  |
|  | 155.1 | 1.18 |  |
| Blank | 205.7 | 1.57 | 0.0 |
|  | 204.7 | 1.56 |  |
|  | 206.6 | 1.58 |  | capability found in these tests. The percent foam increase is determined by dividing the difference between the average wet weight of the cubes containing mixture with foaming agent and average wet weight of the cubes without foaming agent (blanks) by the average wet weight of the blanks.

TEST PROCEDURE II

This procedure was used to compare various foam heights at different temperatures and different percent calcium chloride solutions often used in cement mixtures. The results indicate an increased foam height achieved by the foaming agent compositions of the present invention.

The equipment required for Test Procedure II included a glass Waring blender. The test formula was comprised of deionized water (DI) with various concentrations of CaCl₂·2H₂O solutions (0.4, 4.0, 10.0, 25.0%) and various commercially available foaming agent compositions as comparative examples. The amount of water used must be adjusted to account for the water in the foaming agents of the present invention. 300 grams of DI water alone were initially weighed directly into the Waring blender cup. Varying concentrations of previously prepared CaCl₂·2H₂O solutions were then weighed directly into the Waring blender cup. 0.2% foaming agent was then weighed directly into the blender cup. The mixture was blended for 30 seconds.

After blending, foam height readings (mm) were recorded at the initial time and after 5 minutes. Measurements were made at both 25° C. and 50° C. The results in Table 5 indicate greater foam heights for foaming agent compositions of the present invention as compared to the commercially available foaming agent compositions, particularly at intermediate levels of calcium chloride.

TABLE 5

| CaCl₂·2H₂O % Solution | Foam Heights in Millimeters Initially (Top) and After 5 Minutes (Bottom) When Using: | | | | | |
| --- | --- | --- | --- | --- | --- | --- |
|  | Item 3 | Item 2 | Item 1 | Prod. C | Prod. B | Prod. A |
| Values at 25° C. | | | | | | |
| 0.0 | 115 | 110 | 80 | 95 | 110 | 110 |
|  | 110 | 100 | 70 | 75 | 105 | 100 |
| 0.4 | 115 | 110 | 100 | 100 | 100 | 95 |
|  | 110 | 105 | 90 | 90 | 90 | 85 |
| 4.0 | 110 | 110 | 85 | 90 | 85 | 85 |
|  | 110 | 105 | 85 | 85 | 80 | 85 |
| 10.0 | 90 | 90 | 80 | 85 | 60 | 60 |
|  | 90 | 85 | 75 | 80 | 55 | 60 |
| 25.0 | 45 | 40 | 40 | 40 | 25 | 25 |
|  | 40 | 40 | 40 | 40 | 25 | 25 |
| Values at 50° C. | | | | | | |
| 0.0 | 120 | 120 | 90 | 95 | 125 | 125 |
|  | 100 | 110 | 70 | 60 | 110 | 110 |
| 0.4 | 125 | 125 | 115 | 115 | 115 | 120 |
|  | 115 | 110 | 105 | 100 | 110 | 105 |
| 4.0 | 120 | 120 | 110 | 110 | 85 | 85 |
|  | 110 | 110 | 100 | 95 | 80 | 80 |
| 10.0 | 115 | 110 | 80 | 110 | 80 | 65 |
|  | 110 | 110 | 80 | 100 | 70 | 60 |
| 25.0 | 55 | 45 | 45 | 45 | 25 | 25 |
|  | 45 | 45 | 45 | 40 | 25 | 25 |

What is claimed is:

1. A composition of matter comprising a mixture of molecules conforming the general formula II:

$$CH_3(CH_2)_xCH_2(R)_yOSO_3^-M^+ \quad \text{(II)},$$

wherein x is an integer with a value in the range from about 4 to about 10, R is alkoxy, y is an integer with a value in the range from 0 to about 5, and $M^+$ is chosen from the group consisting of sodium and ammonium ions, wherein the improvement comprises a distribution of molecules conforming to formula II in which not more than 20% by weight of the molecules conform to formula II with y=0 and at least 45% by weight of the molecules conform to formula II with y=2 or 3.

2. A composition according to claim 1, wherein from about 40 to about 60% by weight of the composition consists of molecules conforming to formula II when x has a value in the range from 6 to 8 and R represents an ethoxyl group.

3. A composition according to claim 2, wherein at least 50% by weight of the molecules in the composition that conform to formula II have a value for y of either 2 or 3.

4. A composition according to claim 1, wherein at least 50% by weight of the molecules in the composition that conform to formula II have a value for y of either 2 or 3.

5. A composition according to claim 4, wherein the average value for y in formula II for the molecules conforming to formula II in the composition is about 2.2.

6. A composition according to claim 3, wherein the average value for y in formula II for the molecules conforming to formula II in the composition is about 2.2.

7. A composition according to claim 2, wherein the average value for y in formula II for the molecules conforming to formula II in the composition is about 2.2.

8. A composition according to claim 1, wherein the average value for y in formula II for the molecules conforming to formula II in the composition is about 2.2.

9. A composition according to claim 8, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

10. A composition according to claim 7, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

11. A composition according to claim 6, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

12. A composition according to claim 5, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

13. A composition according to claim 4, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

14. A composition according to claim 3, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

15. A composition according to claim 2, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

16. A composition according to claim 1, consisting essentially of water and:
(A) from about 40 to about 60% by weight of molecules conforming to formula II; and
(B) from about 5 to about 20% by weight of a hydrotrope selected from the group consisting of methanol, ethanol, isopropanol, ethylene glycol, propylene glycols, polyethylene and polypropylene glycols, monoalkyl ethers of ethylene glycol, alkyl polyglucosides, and mixtures thereof; and, optionally,
(C) a sequestering agent for divalent and higher valent metal ions.

* * * * *